(12) United States Patent
Schaffar et al.

(10) Patent No.: US 10,156,544 B2
(45) Date of Patent: Dec. 18, 2018

(54) METHOD AND SYSTEM FOR HYDRATING AND CALIBRATING AN ELECTROCHEMICAL SENSOR

(71) Applicant: Roche Diagnostics Operations, Inc., Indianapolis, IN (US)

(72) Inventors: Bernhard Schaffar, Graz (AT); Robert Poettler, Hartberg (AT); Albert Romann, Zurich (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 193 days.

(21) Appl. No.: 14/931,051

(22) Filed: Nov. 3, 2015

(65) Prior Publication Data

US 2016/0139075 A1    May 19, 2016

(30) Foreign Application Priority Data

Nov. 19, 2014  (EP) ..................................... 14193877

(51) Int. Cl.
| | |
|---|---|
| *G01N 27/327* | (2006.01) |
| *G01N 27/416* | (2006.01) |
| *G01N 33/49* | (2006.01) |

(52) U.S. Cl.
CPC ..... *G01N 27/4163* (2013.01); *G01N 27/3274* (2013.01); *G01N 33/49* (2013.01)

(58) Field of Classification Search
None
See application file for complete search history.

(56) References Cited

U.S. PATENT DOCUMENTS

2006/0180466 A1    8/2006  Dalmia et al.

FOREIGN PATENT DOCUMENTS

WO    2001042473 A3    6/2001

*Primary Examiner* — Gurpreet Kaur
*Assistant Examiner* — Steven E Rosenwald
(74) *Attorney, Agent, or Firm* — Woodard, Emhardt, Moriarty, McNett & Henry LLP

(57) ABSTRACT

Methods and systems for hydrating and calibrating an electrochemical sensor are disclosed. The method comprises providing an electrochemical sensor, providing a calibration solution to a measuring chamber of the electrochemical sensor, contacting the sensor with the calibration solution within the measuring chamber, exposing the sensor and the calibration solution to an elevated temperature, and over a cooling period, cooling the sensor and the calibration solution with a tempering device, wherein the temperature is controllable within a device error range of temperature, performing a plurality of calibrations of the sensor, wherein a calibration of the plurality of calibrations is valid for a calibration margin of temperature error, the calibration margin of temperature error exceeds the device error range of temperature, and controlling a decrease of the temperature of the sensor and the calibration solution not to exceed the calibration margin of temperature error between consecutive calibrations of the sensor.

16 Claims, 6 Drawing Sheets

METHOD AND SYSTEM FOR HYDRATING AND CALIBRATING AN ELECTROCHEMICAL SENSOR

CROSS-REFERENCE TO RELATED APPLICATIONS

This application claims priority to European Patent Application No. 14 193 877.9, filed 19 Nov. 2014, the disclosure of which is hereby incorporated by reference in its entirety.

FIELD OF THE DISCLOSURE

The present disclosure refers to a method and system for hydrating and calibrating an electrochemical sensor.

BACKGROUND

Electrochemical sensors are used in devices for determining an analyte in biological samples. For determining the analyte the sensor needs to be hydrated and calibrated. The process of hydrating may also be referred to as wetting of the sensor or wet-up process.

A hot wetting process for blood gas sensor cartridges is disclosed in International Patent Application Publication No. WO 01/042473 A9. Options for accelerating the hydration of an electrochemical sensor are described. Either a sensor is wetted at an elevated temperature for, e.g., 15 minutes, in a separate device thermostated at temperatures from 55° C. to 75° C. followed by a transfer of the sensor into the instrument sample chamber, which is thermostat-controlled at a lower temperature of 15° C. to 45° C., typically 37° C. Or, the elevated temperature is applied in the measuring chamber of an analyzing device directly. Temperature changes from normal to elevated temperature can be made within 1 to 2 minutes. Although the temperature change is fast, there is a loss of period of use of the instrument, because no calibration or measurement can be performed during this time of temperature change. A calibration, performed at the elevated temperature will not be valid for measurements at a lower temperature level. With regard to sensors for which measurement functionality depends on the sensor temperature, therefore, calibrations have to be repeated at the lower temperature, or no calibration can be performed at the high level temperature. Such concerns are even more present for parameters for which measurement results have to be gathered at fixed or stable temperature conditions. Such parameters are, e.g., pH, $pO_2$ or $pCO_2$.

An abrupt temperature change between both temperature levels causes an obligatory instrument downtime because of the time needed to reach the new thermal equilibrium and the necessary recalibration at the new temperature level.

Also, with the hydration of the sensor matrix, a sensor signal drift is often correlated. Two restrictions are usually present for sensor signal heights. On one hand sensor signals must have a minimum signal height (above a certain signal to noise ratio) to guarantee correct results, as well as sensor signals should not exceed the range of the dynamic range of the electronic signal processing units. In either case non-calibrated sensors will not allow reproducible and reliable measurements with the sensor device.

SUMMARY

It is against the above background that the embodiments of the present disclosure provide certain unobvious advantages and advancements over the prior art. In particular, the inventors have recognized a need for improved technologies for an electrochemical sensor used for determining an analyte in a sample, such as determining an analyte in a biological sample.

In accordance with one embodiment, a method for hydrating and calibrating an electrochemical sensor is provided, comprising: providing an electrochemical sensor; providing a calibration solution to a measuring chamber of the electrochemical sensor; contacting the electrochemical sensor with the calibration solution within the measuring chamber; exposing the electrochemical sensor and the calibration solution to an elevated temperature, comprising elevating the temperature of at least the electrochemical sensor to a hydrating supporting temperature at which hydrating of the electrochemical sensor is facilitated; and, over a cooling period, cooling the electrochemical sensor and the calibration solution with a tempering device, wherein the temperature of the electrochemical sensor and/or the calibration solution is controllable within a device error range of temperature; performing a plurality of calibrations of the electrochemical sensor, wherein a calibration of the plurality of calibrations is valid for a calibration margin of temperature error, and wherein the calibration margin of temperature error exceeds the device error range of temperature; and controlling a decrease of the temperature of the electrochemical sensor and the calibration solution not to exceed the calibration margin of temperature error between consecutive calibrations of the electrochemical sensor.

In accordance with another embodiment, a system for hydrating and calibrating an electrochemical sensor is provided, comprising: an electrochemical sensor; a calibration solution being in contact with the electrochemical sensor within a measuring chamber; a tempering device, configured to temperature controlled cool the electrochemical sensor and the calibration solution, after exposing the electrochemical sensor and the calibration solution to an elevated temperature, over a cooling period, and to control the temperature within a device error range of temperature, wherein the exposing the electrochemical sensor and the calibration solution to the elevated temperature comprises elevating at least the electrochemical sensor to a hydrating supporting temperature at which hydrating of the electrochemical sensor is facilitated; and a measuring device, configured to perform a plurality of calibrations of the electrochemical sensor, wherein a calibration of the plurality of calibrations is valid for a calibration margin of temperature error, the calibration margin of temperature error exceeding the device error range of temperature, wherein the tempering device is further configured to control a decrease of the temperature of the electrochemical sensor and the calibration solution not to exceed the calibration margin of temperature error between consecutive calibrations of the electrochemical sensor.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
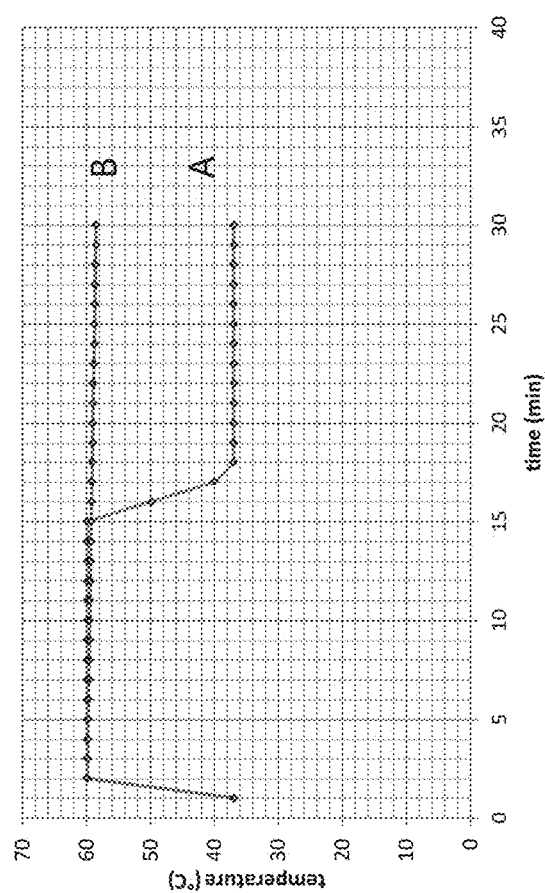
FIG. 1 is a graphical representation of the temperature in dependence on the time with an elevated temperature of about 60° C.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

According to one embodiment of the disclosure, a method for hydrating and calibrating an electrochemical sensor is provided. The method comprises providing an electrochemical sensor, and providing a calibration or calibrating solution. The sensor is contacted with the calibrating solution, thereby, starting hydration of the electrochemical sensor. The electrochemical sensor comprises a measuring chamber. The measuring chamber is designed to receive and contain the sample to be analyzed by the electrochemical sensor and thereby to bring the sample (or other fluids required for the operation of the electrochemical sensor, for example, calibration solutions, quality control solutions, washing and cleaning solutions) into contact with the sensitive regions of the electrochemical sensor. The sensor and the calibrating solution are exposed to an elevated temperature to accelerate the hydration process. Over a cooling period, temperature controlled cooling of the sensor and the calibrating solution is performed by means of a tempering device by which the temperature is controllable within a device error range of temperature, resulting in a corresponding device margin of temperature error. During the cooling period a plurality of calibrations of the sensor is performed using the respective calibrating solutions, wherein a calibration of the plurality of calibrations is valid for a calibration margin of temperature error. The calibration margin of temperature error is exceeding the device margin of temperature error. Due to the smaller device margin of temperature error, a change of the temperature can be controlled with higher accuracy compared to the calibration margin of temperature error. Temperature values being within the calibration margin of temperature error are distinguishable by the temperature control of the tempering device. Compared to the device margin of temperature error, a broader range of error applies to the calibration values with respect to its temperature dependency. A decrease of the temperature of the sensor and the calibration solution is controlled not to exceed the calibration margin of temperature error between consecutive calibrations of the sensor. The change of the temperature between consecutive calibrations is kept within the limits of the calibration margin of temperature error.

According to another embodiment of the disclosure, a system for hydrating and calibrating an electrochemical sensor is provided. The system comprises an electrochemical sensor, and a calibrating solution being in contact with the sensor within a measuring chamber. A tempering device is provided for temperature controlled cooling the sensor and the calibrating solution, after exposing the sensor and the calibrating solution to an elevated temperature, over a cooling period, and for controlling the temperature within a device error range of temperature, resulting in a corresponding device margin of temperature error. A measuring device of the system is configured to perform a plurality of calibrations of the sensor, wherein a calibration of the plurality of calibrations is valid for a calibration margin of temperature error. The calibration margin of temperature error is exceeding the device margin of temperature error. The tempering device is further configured to control a decrease of the temperature of the sensor and the calibration solution not to exceed the calibration margin of temperature error between consecutive calibrations of the sensor.

Measurement signals detected for the calibration process (calibration signals) are detected by the electrochemical sensor using the measuring device also used for gathering measurement signals in the process of determining the analyte.

The wetting process for hydrating the electrochemical sensor may also be referred to as hot wetting. It may be performed in the measuring chamber of an analyzing device configured for determining an analyte in a biological fluid, such as blood glucose characteristics. The hot wetting as proposed here may be performed using rather slow and continuous changes of temperature for both the sensor and the calibration solution.

The performing of the plurality of calibrations may extend over the cooling period as whole or part of it. The plurality of calibrations may be performed while the sensor is used for determining an analyte during the cooling period.

The system for hydrating and calibrating an electrochemical sensor may be provided in an analyzing system for determining an analyte in biological sample. For example, the analyzing system may be configured for determining blood glucose characteristics.

The exposing to the elevated temperature may comprise elevating at least the sensor to a hydrating supporting temperature at which hydrating of the sensor is facilitated. The hydrating supporting temperature may be an elevated temperature compared to one of: room temperature, a normal operating temperature of the sensor, a normal operating temperature of an analytical system comprising the sensor, and a starting temperature being the temperature when the sensor and the calibration solution are contacted. Within the measuring chamber, elevating the sensor to the hydrating supporting temperature will lead to elevating the calibration solution at least in the vicinity of the sensor, specifically the calibration solution being in contact with the sensor, to the hydrating supporting temperature. Other parts of the volume of the calibration solution being outside the vicinity of the sensor may be elevated to the hydrating supporting temperature as well. A heating device may be configured to provide heating to at least one of the sensor and the calibration solution. The heating device may be provided by the tempering device.

The temperature controlled cooling may comprise decreasing the temperature of the sensor and the calibration solution, at least in the vicinity of the sensor, to a normal operating temperature over the cooling period. The normal operating temperature may be defined as a proposed operation parameter of the sensor according to its operation specification. Also, a defined range of temperatures may apply as normal operating temperature.

The process steps of performing the plurality of calibrations and controlling the decrease of the temperature may be performed during a period of time shorter than the cooling period. The period of time may also be equal to the period of time of the cooling period.

The cooling period may be extending over a period of time of at least 10 minutes. In an embodiment, the cooling period may be extending over a period of time of at least 30 minutes, alternatively over a period of time of at least 1 hour. In an alternative embodiment, the cooling period may be extending over a period of time of at least 10 hours, alternatively over a period of at least 20 hours, alternatively over a period of at least 50 hours, and alternatively over a period of at least 100 hours.

The controlling of the decrease of temperature comprises decreasing the temperature of the sensor and the calibration solution by about 0.05 degree Celsius per minute. In an alternative embodiment, decreasing the temperature of the sensor and the calibration solution is done using higher (faster) temperature gradients, e.g., by applying temperature gradients of about 0.1 degree Celsius per minute, or by applying temperature gradients of about 0.5 degree Celsius per minute. In an alternative embodiment, decreasing the temperature of the sensor and the calibration solution is done using lower (slower) temperature gradients, e.g., by applying temperature gradients of about 0.01 degree Celsius per minute, or by applying temperature gradients of about 0.005 degree Celsius per minute.

The controlling of the decrease of temperature may comprise adjusting the decrease of the temperature of the sensor and the calibration solution according to a sensor sensitivity parameter characterizing a temperature-dependent sensitivity of the sensor. The sensor sensitivity parameter may reflect a temperature-dependent signal height at the sensor.

The controlling of the decrease of temperature may comprise adjusting the decrease of the temperature according to a sensitivity parameter characterizing a sensor sensitivity of the electrochemical sensor in dependence on the sensor temperature.

Within a period of time between consecutive calibrations an analyte in at least one of a biological fluid, a control sample, an aqueous solution, and a food sample may be determined by the sensor and an analyzing device coupled to the sensor. The determining may comprise performing one or more measurements. The determining may comprise performing at least one measurement of at least one of a biological fluid, a control sample, an aqueous solution, and a food sample, and at least one measurement of at least one calibration solution, whereby the results of the at least one measurement of at least one of a biological fluid, a control sample, an aqueous solution, and a food sample, and the at least one measurement of the at least one calibration solution is used in the calculation of the analyte result. The determining may comprise determining an analyte in a bodily fluid, e.g., blood glucose characteristics. A method for determining an analyte in at least one of a biological fluid, a control sample, an aqueous solution, and a food sample may be provided, the method including the method for hydrating and calibrating an electrochemical sensor. The determining may refer to determining a parameter selected from the following group: glucose level, lactate, creatinine, urea, and components like Na, K, and Cl. Different fluids may be determined, e.g., plasma, serum, urine, saliva, or cerebrospinal fluid (CSF).

The providing may comprise providing an aqueous calibration solution.

The contacting may comprise the calibration solution at an elevated temperature flowing over the sensor. The flowing solution may be applied via fluidic channels on the surface of the sensor and thus directly heating an active zone of the electrochemical sensor.

FIG. 1 shows a graphical representation of the temperature in dependence on the time for a period of time of a hydrating process of an electrochemical sensor. Like known as such, the sensor is brought in contact with a fluid for hydrating the dry sensor (wetting up). Both the sensor and the fluid, for example a calibration fluid provided in the analyzing device using the sensor, are exposed to an elevated temperature for supporting the hydration.

Referring to FIG. 1, curve A represents a curve progression known from the prior art. Curve B represents a temperature curve progression characterized by a slow continuous decrease over the time period of observation. For both curve A and curve B, at the beginning there is a rapid increase in temperature. Such increase represents starting exposure of a sensor and a calibrating solution being in contact with the sensor to an elevated temperature for supporting hydration of the sensor. The elevated temperature is about 60° C. in FIG. 1. After a period of about 15 minutes a cooling period is started characterized by lowering the temperature applied to the sensor and the calibrating solution. With respect to curve A, there is a sharp drop of the temperature. In contrast, referring to curve B, the temperature is decreased continuously in rather small steps.

Figure 2:
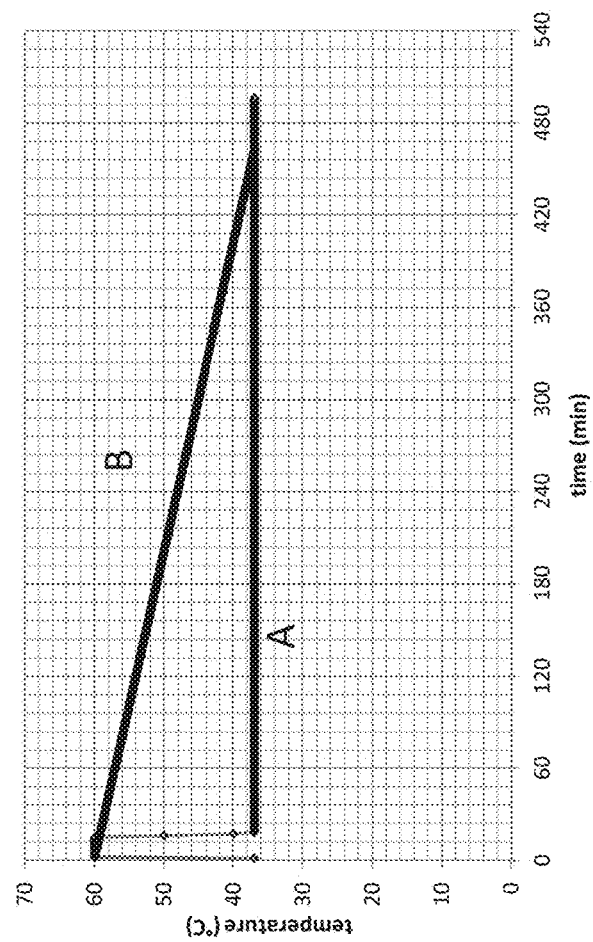
FIG. 2 is a graphical representation of the temperature in dependence on the time, compared to FIG. 1, on a longer time scale.

FIG. 2 shows a graphical representation of the temperature progression in dependence on the time, compared to FIG. 1, on a longer time scale. Finally, at the end of the cooling period a temperature of about 37° C. is reached. However, for the process reflected by curve B this takes about 460 minutes. A temperature decrease of 0.05° C. per minute is assumed.

With respect to the method reflected by curve B, the cooling period is characterized by a defined continuous decrease, so that drift of sensor signal height remains insignificantly low and well within the error limits between calibrations and measurements.

A rate of continuous lowering of the temperature may be calculated by using three parameters: the temperature specification of the measurement chamber (tempering device), the temperature difference between the elevated temperature applied for supporting hydration of the sensor and the temperature after the cooling period, and the maximum allowed interval of time between consecutive calibrations. As an example, the following parameters may be assumed: +/−0.2° C. precision of the temperature control, a calibration interval of 1 hour, and a temperature difference of 15° C. This will result in a time span for the continuous temperature drop of 15° C.*1 h/0.2° C.=75 h.

Figure 3:
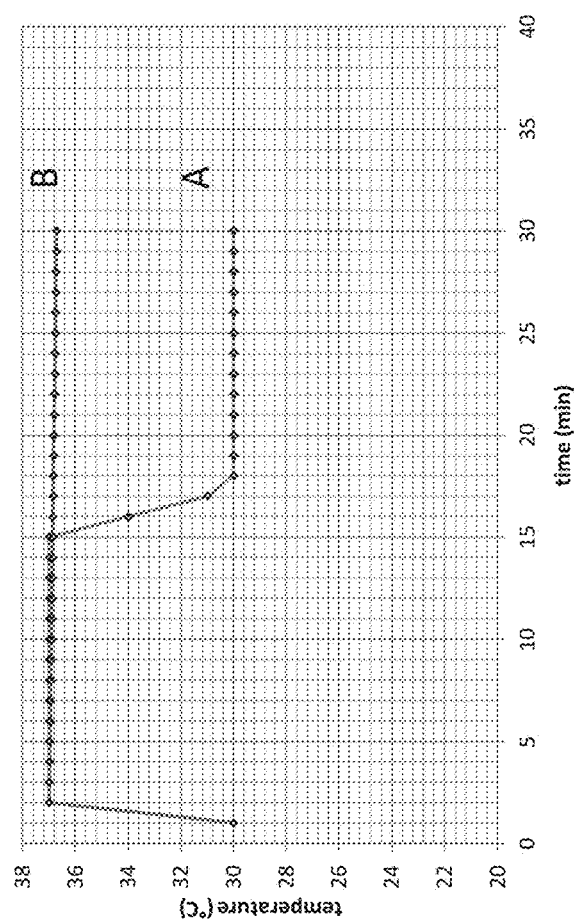
FIG. 3 is a graphical representation of the temperature in dependence on the time with an elevated temperature of about 37° C.
Figure 4:
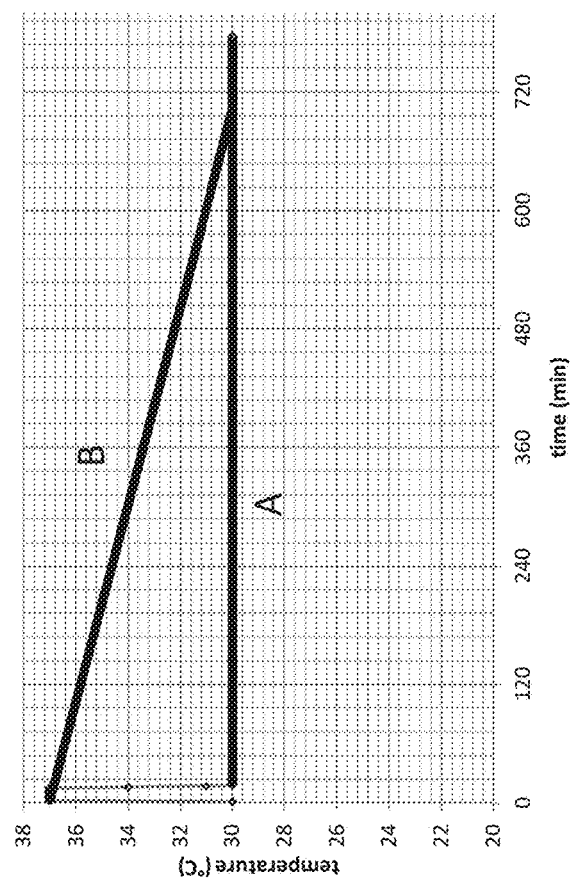
FIG. 4 is a graphical representation of the temperature in dependence on the time, compared to FIG. 3, on a longer time scale.

In case of a temperature drop from 37° C. (elevated temperature) to 30° C., with a calibration interval of 0.5 hour, there will be an 11.5 hour time span for the temperature drop during the cooling period (see FIG. 3 and FIG. 4). A temperature decrease of 0.01° C. per minute is assumed.

Referring to FIGS. 1 to 4, the sensor and the calibrating solution are exposed to an elevated temperature for a relatively short period of time. Over the following cooling period, temperature controlled cooling of the sensor and the calibrating solution, which is in contact with the sensor, is performed by means of a tempering device by which the temperature is controllable within a device error range of temperature, resulting in a corresponding device margin of temperature error. Within this period of temperature controlled cooling, a plurality of calibrations of the sensor may be performed, wherein a calibration of the plurality of calibrations is valid for a calibration margin of temperature error, the calibration margin of temperature error exceeding the device margin of temperature error. Due to the smaller device margin of temperature error, a change of the temperature can be controlled with higher accuracy compared to the calibration margin of temperature error. Temperature values being within the calibration margin of temperature error are distinguishable by the temperature control of the tempering device. Compared to the device margin of temperature error, a broader range of error applies to the calibration values with respect to its temperature dependency. A decrease of the temperature of the sensor and the calibration solution is controlled not to exceed the calibration margin of temperature error between consecutive calibrations of the sensor. The change of the temperature between consecutive calibrations is kept within the limits of the calibration margin of temperature error.

With respect to the analyzing device in which the sensor is to be used, there is minimized downtime of the analyzing device, because the continuous temperature drop allows permanent operation also during the cooling phase.

In the case of sensor signals drifting to higher levels during hydration, the continuous temperature drop can linearize the calibration function, and allows therefore less frequent calibration cycles, resulting in more time for sample measurements.

Figure 5:
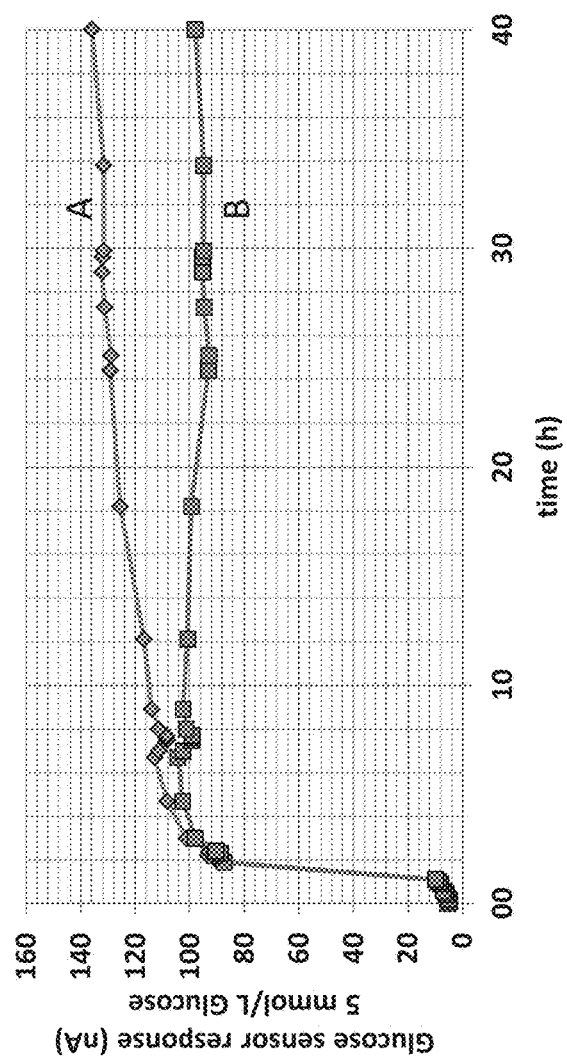
FIG. 5 is a graphical representation of the signal of an electrochemical glucose sensor in dependence on the time.

FIG. 5 shows an improvement in sensor drift behavior if the normal sensor wet-up for sensor hydration is performed at a constant temperature of 37° C. Curve A represents measured values. There is sensor signal drift towards higher values (from about 100 nA to about 135 nA) in the time range between 3 hours and 40 hours. As for curve B, a drift of the temperature function of the glucose sensor (4% signal decrease per ° C.) was applied to the measured signals of curve A. The starting temperature is 37° C., and, after the cooling period, the end temperature is 30° C. This results in a more stable sensor signal (about 100 nA), especially in the time interval between 3 hours and 40 hours. Curve B was calculated by subtracting a temperature effect from the measured values of curve A for a temperature decrease from 37° C. to 30° C. over a time period of 25 hours applying a linear temperature coefficient of 4% per degree Celsius.

A temperature decrease optimum can be derived from the necessary temperature gap, for example, between 37° C. and 30° C., the known temperature dependence of the sensor, for example, 4% sensor signal height (decrease/increase) per degree Celsius for glucose or lactate sensors, as well as stability data of the corresponding sensors.

Figure 6:
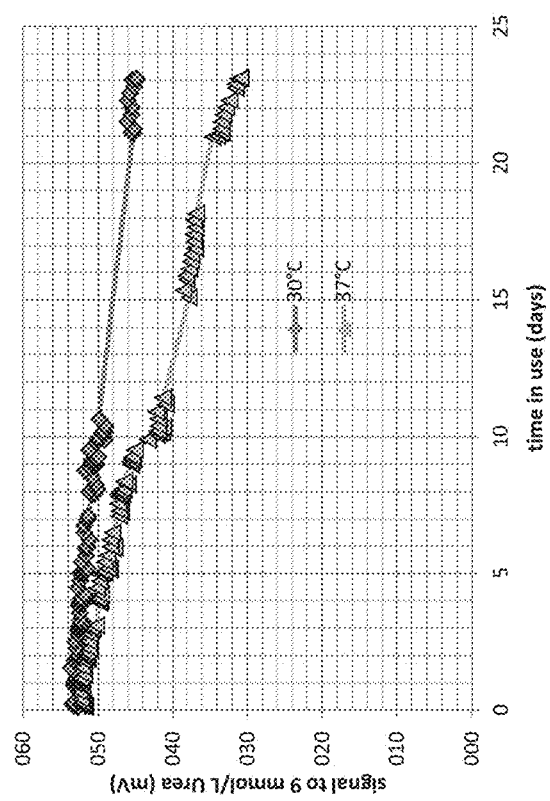
FIG. 6 is a graphical representation of the signal of an urea sensor in dependence on the time at different temperatures.

An example illustrating the dependency of a sensor signal over time (corresponds to the term stability) from the temperature is given in FIG. 6. It shows the measurement signal of an electrochemical urea sensor over time at constant temperatures of 30° C. and 37° C., respectively. Even if the urea concentration is identical for both temperatures (9 mmol/L) the loss in signal height at 30° C. is significantly less than at 37° C. over time. This effect is mainly caused by the temperature dependent activity loss of the enzyme (in this example: urease) in this type of sensor. This comparison of the sensor signals over time at constant temperatures of 30° C. and 37° C., respectively, shows that it may be advantageous to reduce the temperature to lower values after the initial wet-up phase because an operation at lower temperatures reduces the loss of enzyme activity over time and thereby increases the overall period of use of the sensor.

Thus, a combination of a short initial wet-up initiation at higher temperatures with a subsequent period of sensor usage at lower temperatures can be advantageous for the overall lifetime of the sensor. These effects in combination with the cooling phase provided with a relatively slow cooling rate lead to a maximized operating state of the sensor in which the sensor can be used for sample measurements.

In principle, a temperature change can be regulated according to a fixed program, a so called temperature ramp, such as shown in FIGS. 1 to 4 (curve B).

In alternative embodiments, which may differ from the embodiments given above, a temperature regulation according to, e.g., the sensor signal height, can also be considered. For example, if the sensor is operated in a limited gain range it could be advantageous to adjust the signal height of the sensor to the typical gain range by increasing or decreasing the temperature of the sensor. By superposition of this additional temperature alignment with the temperature decrease in the cooling period as described above, an even more stable sensor signal could be achieved and, as a consequence of such a more stable sensor signal, longer calibration intervals are possible, resulting in an even longer operating state of the sensor in which the sensor can be used for sample measurements.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A method for hydrating and calibrating an electrochemical sensor, comprising:
   providing an electrochemical sensor,
   providing a calibration solution to a measuring chamber of the electrochemical sensor,
   contacting the electrochemical sensor with the calibration solution within the measuring chamber,
   raising the temperature of the electrochemical sensor and the calibration solution to an elevated temperature by exposing the electrochemical sensor and the calibration solution to an elevated temperature, comprising elevating the temperature of at least the electrochemical sensor to a hydrating supporting temperature at which hydrating of the electrochemical sensor is facilitated, and over a cooling period comprising reducing the temperature of the electrochemical sensor and the calibration solution from the elevated temperature to a reduced temperature,
  cooling the electrochemical sensor and the calibration solution with a tempering device, wherein the temperature of the electrochemical sensor and/or the calibration solution is controllable within a device error range of temperature,
  performing a plurality of calibrations of the electrochemical sensor at different temperatures as the temperatures of the electrochemical sensor and the calibration solution are reduced from the elevated temperature to the reduced temperature, wherein a calibration of the plurality of calibrations is valid for a calibration margin of temperature error, and wherein the calibration margin of temperature error exceeds the device error range of temperature, and
  controlling the reducing of the temperature of the electrochemical sensor and the calibration solution not to exceed the calibration margin of temperature error between consecutive calibrations of the electrochemical sensor.

2. The method according to claim 1, wherein the cooling comprises reducing the temperature of the electrochemical sensor and the calibration solution to an operating temperature of the electrochemical sensor over the cooling period.

3. The method according to claim 1, wherein the cooling period is extending over a period of time of at least 10 minutes.

4. The method according to claim 1, wherein controlling the reducing of the temperature comprises reducing the temperature of the electrochemical sensor and the calibration solution by about 0.05 degrees Celsius per minute.

5. The method according to claim 1 further comprising within a period of time between consecutive calibrations, determining an analyte in at least one of a biological fluid, a control sample, an aqueous solution, and a food sample by the electrochemical sensor and an analyzing device coupled to the electrochemical sensor.

6. The method according to claim 1, wherein providing the calibration solution comprises providing an aqueous calibration solution.

7. The method according to claim 1, wherein contacting the electrochemical sensor with the calibration solution comprises the calibration solution flowing over the electrochemical sensor.

8. The method according to claim 1, wherein the cooling period extends over a period of time of at least one hour.

9. The method according to claim 8, wherein the cooling period extends over a period of time of at least ten hours.

10. The method according to claim 1, wherein controlling the reducing of the temperature comprises reducing the temperature of the electrochemical sensor and the calibration solution by about 0.5 degrees Celsius per minute or lower.

11. The method according to claim 10, wherein controlling the reducing of the temperature comprises reducing the temperature of the electrochemical sensor and the calibration solution by about 0.1 degrees Celsius per minute or lower.

12. The method of claim 1 in which during the cooling period the temperature controlled cooling comprises reducing the temperature of the electrochemical sensor and the calibration solution to at least 37 degrees Celsius.

13. The method of claim 1 in which the calibrations are performed at intervals from 0.5 per hour to 1 per hour.

14. A system for hydrating and calibrating an electrochemical sensor, comprising:
  an electrochemical sensor,
  a calibration solution being in contact with the electrochemical sensor within a measuring chamber,
  a tempering device, configured to temperature controlled cool the electrochemical sensor and the calibration solution, by exposing the electrochemical sensor and the calibration solution to an elevated temperature, over a cooling period, and to control the temperature within a device error range of temperature, the exposing the electrochemical sensor and the calibration solution to the elevated temperature comprising elevating at least the electrochemical sensor to a hydrating supporting temperature at which hydrating of the electrochemical sensor is facilitated, the cooling comprising reducing the temperature of the electrochemical sensor and the calibration solution from the elevated, hydrating supporting temperature to a reduced temperature, and
  a measuring device, configured to perform a plurality of calibrations of the electrochemical sensor at different temperatures as the temperature of the electrochemical sensor and the calibration solution are reduced from the elevated temperature to the reduced temperature, wherein a calibration of the plurality of calibrations is valid for a calibration margin of temperature error, the calibration margin of temperature error exceeding the device error range of temperature,
  wherein the tempering device is further configured to control a reducing of the temperature of the electrochemical sensor and the calibration solution not to exceed the calibration margin of temperature error between consecutive calibrations of the electrochemical sensor.

15. A method for hydrating and calibrating an electrochemical sensor, comprising:
  providing an electrochemical sensor;
  providing a calibration solution to a measuring chamber of the electrochemical sensor;
  contacting the electrochemical sensor with the calibration solution within the measuring chamber;
  exposing the electrochemical sensor and the calibration solution to an elevated temperature, comprising elevating the temperature of at least the electrochemical sensor to a hydrating supporting temperature at which hydrating of the electrochemical sensor is facilitated; and
  over a cooling period
  temperature controlled cooling of the electrochemical sensor and the calibration solution by means of a tempering device by which the temperature is continuously reduced and controllable within a device error range of temperature,
  performing a plurality of calibrations of the electrochemical sensor while the temperature is continuously reduced from the elevated temperature, wherein a calibration of the plurality of calibrations is valid for a calibration margin of temperature error, the calibration margin of temperature error exceeding the device margin of temperature error, and
  controlling the continuous reducing of the temperature of the electrochemical sensor and the calibration solution not to exceed the calibration margin of temperature error between consecutive calibrations of the electrochemical sensor.

16. A method for hydrating and calibrating an electrochemical sensor, comprising:

providing an electrochemical sensor having a measuring chamber;

providing a calibration solution to the measuring chamber;

elevating the temperature of at least the electrochemical sensor to a hydrating supporting temperature at which hydrating of the electrochemical sensor is facilitated;

cooling the electrochemical sensor from the elevated temperature to a reduced temperature by means of a tempering device; and during said cooling, performing a plurality of calibrations of the electrochemical sensor at different temperatures and with temperature differentials between successive calibrations, the temperature difference between successive calibrations being such that each calibration has a calibration margin of temperature error that overlaps the calibration margin of temperature error of the succeeding calibration.

\* \* \* \* \*